United States Patent [19]

Lafon

[11] Patent Number: 5,128,349
[45] Date of Patent: Jul. 7, 1992

[54] 1-(4-AMINOPHENYL)-2-PIPERIDINO-PROPANONE DERIVATIVES, PREPARATION PROCESS AND USE IN THERAPEUTICS

[75] Inventor: Louis Lafon, Paris, France

[73] Assignee: Laboratoire L. Lafon, Maisons Alfort, France

[21] Appl. No.: 604,802

[22] Filed: Oct. 29, 1990

[30] Foreign Application Priority Data

Oct. 30, 1989 [FR] France ............................ 89 14217

[51] Int. Cl.$^5$ .................. A61K 31/445; C07D 211/14
[52] U.S. Cl. ...................................... 514/331; 546/235
[58] Field of Search ......................... 546/235; 514/331

[56] References Cited

U.S. PATENT DOCUMENTS

| 3,536,712 | 10/1970 | Keck et al. ........................ 564/363 |
| 3,772,275 | 11/1973 | Hernestam et al. ................ 544/165 |
| 4,282,206 | 8/1981 | Warner, Jr. et al. ................ 424/59 |
| 4,980,377 | 12/1990 | Lafon ................................. 514/649 |

FOREIGN PATENT DOCUMENTS

| 0138714 | 10/1984 | European Pat. Off. . |
| A20174242 | 3/1986 | European Pat. Off. . |
| 2569184 | 2/1986 | France . |
| 1180890 | 2/1970 | United Kingdom . |

OTHER PUBLICATIONS

Lafon[2], CA 105: 17055z (abstract only).

Primary Examiner—Allen J. Robinson
Assistant Examiner—Shailendra Kumar
Attorney, Agent, or Firm—Wegner, Cantor, Mueller & Player

[57] ABSTRACT

The present invention relates to 1-(4-aminophenyl)-2-piperidinopropanone derivatives which are selected from
(a) the compounds corresponding to the general formula

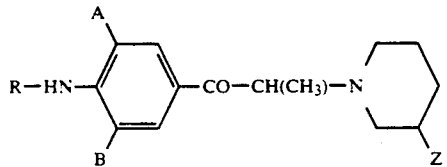

where R is H or $CH_3CO$, A is H or Cl, B is H or Cl and Z is $C_1$-$C_4$-alkyl; and
(b) their addition salts, These products are used as cardiovascular agents. In particular, the compounds of the formula I where R=H or $CH_3CO$, A=B=Cl and Z=$CH_3$, and their addition salts, are especially very worthwhile as vasodilators.

10 Claims, No Drawings

1-(4-AMINOPHENYL)-2-PIPERIDINOPROPANONE DERIVATIVES, PREPARATION PROCESS AND USE IN THERAPEUTICS

INTRODUCTION

The present invention relates to 1-(4-aminophenyl)-2-piperidinopropanone derivatives. It also relates to a process for the preparation of these products and to their use in therapeutics in the cardiovascular field.

PRIOR ART

In EP-A-0 138714 1-(acetylaminophenyl)-2-aminopropanone derivatives of the formula

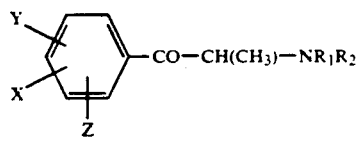

have been described in which, in particular, $R_1$ and $R_2$, considered together, may form, with the nitrogen atom to which they are bonded, a 5 to 7-membered N-heterocyclic group capable (i) of containing a second hetero-atom, in particular selected from N, O and S, and (ii) of being substituted, the said heterocyclic group $NR_1R_2$ being, in particular, selected from the group consisting of the pyrrolidino, morpholino, thiomorpholino, piperidino, hexamethyleneimino, piperazino, 4-methylpiperazino, 4-($\beta$hydroxyethyl)-piperazino, 4-phenylpiperazino and 4-(p-chlorophenyl)-piperazino groups;

and X is $CH_3CONH$ and Y and Z, which may be identical or different, each represent a hydrogen or halogen atom.

These compounds have been described as antidepresants of the central nervous system.

In EP-A-0 174 242 1-(4-aminophenyl)-2-aminopropanone derivatives of the formula Io

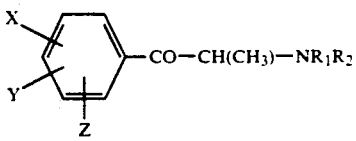

have been described in which, in particular,

X is $NH_2$,

Y and Z, which may be identical or different, represent a hydrogen or halogen atom and $R_1$ and $R_2$, considered together, may form, with the nitrogen atom to which they are bonded, a 5 to 7-membered N-heterocyclic group which can contain a second hetero-atoms elected from N, O and S and can be substituted, the said heterocyclic group $NR_1R_2$ being selected from the group comprising the pyrrolidino, morpholino, thiomorpholino, piperidino, hexamethyleneimino, piperazino, 4-methylpiperazino, 4-phenylpiperazino, 4-(2-hydroxyethyl)-piperazino and 4-(p-chlorophenyl)-piperazino groups.

These compounds have also been described as antidepressants of the central nervous system.

SUMMARY OF THE INVENTION

According to the invention new compounds belonging to the family of the 1-(aminophenyl)-2-aminopropanone derivatives and a process for their preparation are provided, these new products being particularly useful in therapeutics.

These new compounds are distinguished by vasodilative effects beneficial in diseases of the cardiovascular system, these being effects of which the most closely related compounds described in EP-A-0 174 242 and EP-A-0 138 714 are devoid.

The compounds according to the invention are characterized in that they are selected from (a) the compounds corresponding to the general formula

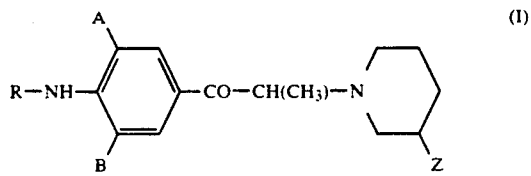

where R is H or $CH_3CO$, A is H or Cl, B, independently of A, is H or Cl and Z is a $C_1-C_4$-alkyl group; and (b) their addition salts.

DETAILED DESCRIPTION OF THE INVENTION

Amongst the $C_1-C_4$-alkyl groups which occur in the definition of Z, those which may be mentioned are the straight or branched chain hydrocarbon radicals having at most four carbon atoms, such as $CH_3$, $CH_2CH_3$, $CH_2CH_2CH_3$, $CH_2CH_2CH_2CH_3$, $CH(CH_3)_2$ and $C(CH_3)_3$.

Here, addition salts are understood to be the acid addition salts obtained by reaction of a free base of formula I with an inorganic or organic acid, on the one hand, and the ammonium salts on the other hand. Amongst the acids which can be used to convert the free base of formula I to a salt, those which may be mentioned in particular are hydrochloric, hydrobromic, acetic, formic, propionic, oxalic, fumaric, maleic, succinic, benzoic, cinnamic, mandelic, citric, malic, tartaric, aspartic, glutamic, methanesulphonic and p-toluenesulphonic acids. Amongst the compounds which enable ammonium salts to be obtained, those which may be mentioned in particular are $ICH_3$ and $ClCH_3$. In general, the acid addition salts, such as, in particular, the hydrochlorides, are preferred to the ammonium salts.

The invention relates in particular to 1-(4-aminophenyl)-2-(3-methylpiperidino)propanone, 1-(4-acetylaminophenyl)-2-(3-methylpiperidino)propanone, 1-(4-amino-3,5-dichlorophenyl)-2-(3-methylpiperidino)propanone, 1-(4-acetylamino-3,5-dichlorophenyl)-2-(3-methylpiperidino)propanone and their addition salts.

Some compounds according to the invention have been listed, without any limitation being implied, in Table I below, with, for comparison, the two homologues CP-1 and CP-2 described in the aforementioned documents, which are CNS antidepressants and stimulants but which do not have cardiovascular effects.

TABLE I

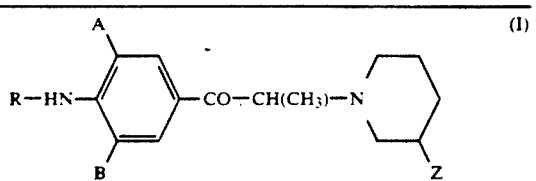

| Example | Code No. | R | A | B | Z |
|---|---|---|---|---|---|
| Ex 1 (a) | CRL 41 419 | CH₃CO | 3-Cl | 5-Cl | CH₃ |
| Ex 2 (a) | CRL 41 418 | H | 3-Cl | 5-Cl | CH₃ |
| Ex 3 (b) | CRL 41 419A | CH₃CO | 3-Cl | 5-Cl | CH₃ |
| Ex 4 (a) | CRL 41 416 | CH₃CO | H | H | CH₃ |
| Ex 5 (c) | — | H | H | H | CH₃ |
| CP-1(c,d) | CRL 41 241 | H | H | H | H |
| CP-2(a,e) | CRL 41 240 | CH₃CO | H | H | H |

Notes.
(a) monohydrochloride
(b) methanesulphonate
(c) dihydrochloride
(d) described in Example 11 of EP-A-0 174 242
(e) described in Example 11 of EP-A-0 138 714

The compounds of formula I can be prepared by a method known per se, by application of conventional reaction mechanisms.

In particular, they can be synthesized according to the operating methods described in the abovementioned patent documents EP-A-0 174 242 and EP-A-0 138 714.

The process which is specified here consists in reacting a 3-alkylpiperidine of formula

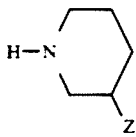

in which Z is a $C_1$-$C_4$-alkyl group as defined above, with a 1-(4-aminophenyl)-2-halogenopropanone of formula

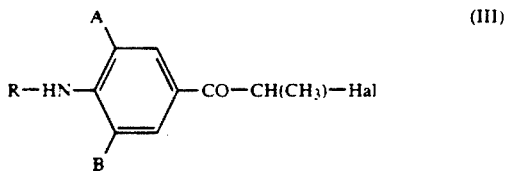

in which R, A and B are defined as indicated above and Hal represents a halogen atom (in particular F, Cl and Br, the preferred halogen atom here being chlorine).

The reaction II+III applies to the synthesis of all of the compounds of formula I above. Advantageously 0.2 to 0.3 mol of compound III will be used per 1 mol of compound of formula II, for at least 0.5 h, at a temperature between ambient temperature (15°–25° C.) and the reflux temperature of the reaction medium. In this reaction, compound II is involved either as solvent or even better as co-solvent.

As a variant, each compound of formula I where R=CH₃CO can be prepared by acetylation of the corresponding compound of formula I where R=H in accordance with an acetylation method known per se. From this point of view, 0.2 to 0.4 mol of compound of formula I where R=H will be reacted with 1 mol of acetyl halide, preferably acetyl chloride (the chlorine atom being the preferred halogen atom as indicated above). In this variant, acetic acid is generally involved as solvent.

The compounds according to the invention have beneficial therapeutic properties. They act in particular at the cardiovascular level and have vasodilative effects which are unexpected having regard to the teaching of the abovementioned European Patents EP-A-0 138 714 and EP-A-0 174 242, since the comparison products CP-1 and CP-2 are devoid of cardiovascular effects and act essentially as CNS antidepressants.

The most valuable compounds according to the invention as vasodilators are 1-(4-amino-3,5-dichlorophenyl)-2-(3-methylpiperidino)propanone, 1-(4-acetylamino-3,5-dichlorophenyl)-2-(3-methylpiperidino)propanone and their non-toxic addition salts.

According to the invention, a therapeutic composition is specified which is characterized in that it contains, in combination with a physiologically acceptable excipient, at least one derivative selected from the compounds of formula I and their non-toxic addition salts.

Of course, in such a composition the active principle, that is to say the compound of formula I or one of its non-toxic salts, is present in a pharmaceutically effective amount.

According to the invention, the use of a substance selected from the group comprising (i) 1-(4-amino-3,5-dichlorophenyl)-2-(3-methylpiperidino)propanone, (ii) 1-(4-acetylamino-3,5-dichlorophenyl)-2-(3-methylpiperidino]propanone and (iii) their non-toxic addition salts is specified for obtaining a vasodilative medicament intended for use in human therapy against diseases of the cardiovascular system, in particular diseases such as infarction which involve the administration of a coronary vasodilator, on the one hand, and circulation disorders of the brain and the extremities which imply the administration of a peripheral vasodilator, on the other hand.

Other advantages and characteristics of the invention will be better understood on reading the following preparation examples and results of pharmacological studies, all of these aspects being in no way limiting but being given by way of illustration.

PREPARATION I

Production of 1-(4-amino-3,5-dichlorophenyl)-2-(3-methylpiperidino)-propanone monohydrochloride (Example 2; Code No.: CRL 41 418)

Other nomenclature: α-(3-methylpiperidino)-4-amino-3,5-dichloropropiophenone monohydrochloride a) 1-(4-acetylaminophenyl)-2-chloropropanone An amount of 118 g (0.93 mol) of 2-chloropropionyl chloride is run, in the course of 1.5 h, into a mixture of 69.2 g (0.50 mol) of acetanilide and 205 g (1.50 mol) of aluminium chloride in 525 ml of carbon disulphide and the mixture is refluxed for 1 h. The supernatant liquor is decanted off and the residue is hydrolysed with 1900 ml of ice-water and 385 ml of 4N hydrochloric acid. The precipitate formed is isolated by filtration and taken up in benzene, which is distilled azeotropically by means of a Dean-Stark apparatus. After treating the hot solution with carbon black (CXA) and cooling, 102.4 g (yield: 90.82 %) of the expected product are isolated in the form of a slightly beige powder.

m.p.$_{inst.}$ (Kofler)=120° C.

b) 1-(4-aminophenyl)-2-chloropropanone

A mixture of 102 g (0.45 mol) of 1-(4-acetylaminophenyl)-2-chloropropanone in 400 ml of 6N HCl acid is refluxed for 1.5 h. The resulting solution is treated, while still hot, with carbon black and neutralized with ammonia. The precipitate formed is isolated by filtration and taken up in benzene, which is distilled azeotropically. After treating the residual solution, while still hot, using carbon black, the product is allowed to crystallize and 65 g (yield: 78.7 %) of the expected product, which is in the form of a beige coloured powder, are recovered by filtration.

m.p.$_{inst.}$ (Kofler) = 100°–102° C.

c) 1-(4-amino-3,5-dichlorophenyl)-2-chloropropanone

An amount of 72 g (0.54 mol) of N-chlorosuccinimide is introduced in fractions in the course of 1 h into a solution of 33 g (0.18 mol) of 1-(4-aminophenyl)-2-chloropropanone in 180 ml of carbon tetrachloride, kept at 70° C. The reaction mixture is diluted with 200 ml of chloroform, the insoluble matter formed is removed by filtration and the filtrate is then brought to dryness under reduced pressure. The evaporation residue thus obtained is taken up in diethyl ether and the insoluble matter which results is removed by filtration and the solvent is removed by distillation. The residual brown mass is. purified by recrystallization from isopropanol. 30.8 g (yield:.67.8 %) of the expected product, which is in the form of a white powder are obtained.

m.p.$_{inst.}$ (Kofler) = 110°–112° C.

d) CRL 41 418

A mixture of 25.25 g (0.10 mol) of 1-(4-amino-3,5-dichlorophenyl)-2-chloropropanone and 50 g (0.50 mol) of 3-methylpiperidine in 60 ml of water is stirred for 0.5 h at ambient temperature (15°–20° C.) and then for 0.5 h at 70° C. The reaction mixture is diluted with 100 ml of water, the resulting mixture is extracted with ethyl acetate and the ethyl acetate phase is then extracted using a dilute aqueous HCl solution. After neutralizing the aqueous phase thus obtained, using ammonia, it is extracted with diethyl ether and the ethereal solution is then treated with ethanol containing HCl acid. Oily insoluble matter forms, which is subjected to a washing operation using acetone and then to purification by recrystallization from an acetonitrile/isopropanol (4/1) v/v mixture. 19.6 g (yield: 55.8%; total yield from steps a–d; 27%) of the expected product, which is in the form of a beige powder which is soluble in water in a concentration of 50 g/l, are thus obtained.

m.p. = 200°–220° C. (with decomposition).

PREPARATION II

Production of 1-(4-acetylamino-3,5-dichlorophenyl)-2-(3-methylpiperidino)propanone monohydrochloride (Example 1; Code No.: CRL 41 419)

Other nomenclature: 6ω-(3-methylpiperidino)-4-acetamido-3,5-dichloropropiophenone monohydrochloride.

A solution comprising 13.5 g (0.035 mol) of 1-(4-amino-3,5-dichlorophenyl)-2-(3-methylpiperidino)-propanone monohydrochloride and 8.2 ml (0.114 mol) of acetyl chloride in 50 ml of acetic acid is stirred overnight at ambient temperature. The reaction mixture is evaporated to dryness under reduced pressure and the evaporation residue thus obtained is purified by washing in acetone.

15 g (yield: about 100 %) of the expected product, which is in the form of a slightly beige coloured powder, are obtained.

m.p. = 220° C. (with decomposition).

PREPARATION III

Alternative method for obtaining 1-(4-acetylamino-3,5-dichlorophenyl)-2-(3-methylpiperidino)propanone monohydrochloride (Example 1; Code No.: CRL 41 419)

CRL 41 419 is obtained by carrying out the procedure as indicated in Preparation Id but replacing 1-(4-amino-3,5-dichlorophenyl)-2-chloropropanone by 1-(4-acetylamino-3,5-dichlorophenyl)-2-chloropropanone.

m.p. = 220° C. (with decomposition).

PREPARATION IV

Production of 1-(4-acetylaminophenyl)-2-(3-methylpiperidino)propanone monohydrochloride (Example 4; Code No.: CRL 41 416)

A mixture comprising 60 g (0.266 mol) of 1-(4-acetylaminophenyl)-2-chloropropanone [product obtained by the procedure of Preparation Ia], 100 g (1.0 mol) of 3-methylpiperidine and 100 ml of water is stirred for 24 h at ambient temperature. The reaction mixture is diluted with 250 ml of water and the insoluble matter is extracted using ethyl acetate. The ethyl acetate phase is washed with 3×500 ml of water. The ethyl acetate phase is dried over anhydrous sodium sulphate and ethanol containing hydrochloric acid is then added, with stirring. The precipitate formed is recovered by filtration and purified by recrystallization from an isopropanol/ethanol (5/4) v/v mixture to give 66.3 g (yield: 76.8 %) of the expected product, which is in the form of a white powder soluble in water.

m.p. = 230° C. (with decomposition).

The results of toxicological, neuropsychopharmacological and cardiovascular studies which were undertaken with the compounds according to the invention are summarized below.

A. STUDIES RELATING TO CRL 41 419 (PRODUCT FROM EXAMPLE 1)

TOXICOLOGICAL STUDY

In the toxicological and neuropsychopharmacological studies which follow, CRL 41 419, in solution in distilled water, was administered intraperitoneally in a volume of 20 ml/kg to male mice and of 5 ml/kg to male rats. The pH of the solution varies as a function of the CRL 41 419 concentration; it ranges from 4.5 for a concentration of 50 g/l to 5 for a concentration of 12.5 g/l and to 5.5 for concentrations of less than or equal to 6.4 g/l.

Toxicity

In male mice the LD-0 (maximum non-lethal dose) intraperitoneally is higher than 256 mg/kg and the LD-100 (minimum dose lethal for all the animals treated) is of the order of 512 mg/kg (at this dose the death of the mice occurs within 0.5–4 h from the administration of CRL 41 419).

Neuropsychopharmacological Study

OVERALL BEHAVIOUR AND REACTIVITIES

Groups of three animals are observed before and then 0.25 h, 0.50 h, 1 h, 2 h, 3 h and 24 h after administration of CRL 41 419. The findings are as follows:
1) in mice
   for doses of 2 mg/kg, 4 mg/kg and 8 mg/kg:
   behaviour and reactivities substantially comparable to those of the control group;
   for a dose of 32 mg/kg:
   hypothermia ($-1°$ C.) for 2 hours;
   for a dose of 128 mg/kg:
   sedation for 0.5 h;
   hypothermia for 3 h (maximum value: $-3.7°$ C., 30 minutes after administration);
   a reduction in the reactivity to the touch, in the muscular tonus and in the aggressivity reaction; and
2) in rats
   for doses of 1 mg/kg, 2 mg/kg, 4 mg/kg and 16 mg/kg:
   behaviour, reactivities and a variation in the rectal temperature and in the pupil diameter substantially comparable to those of the control group;
   for a dose of 64 mg/kg:
   sedation for 0.25 h accompanied by a reduction in the heart rate.

Cardiovascular Study

In the cardiovascular study, CRI, 41 419 was administered in solution in isotonic sodium chloride solution (NaCl concentration: 9 g/l in water), at pH 3.3, the maximum concentration of the said CRL 41 419 having been used being 66 g/l.

I. Intraduodenal Administration

Three male dogs having an average weight of 13.6 kg, anaesthetized with nembutal, receive CRL 41 419 intraduodenally in successive doses of 0 mg/kg (each animal serving as control with respect to itself); 0.55 mg/kg; 1.1 mg/kg; 2.75 mg/kg; 5.5 mg/kg; 11 mg/kg; and 22 mg/kg respectively [doses corresponding to 0; 0.5 mg/kg; 1 mg/kg; 2.5 mg/kg; 5 mg/kg; 10 mg/kg; and 20 mg/kg respectively of 1-(4-acetylamino-3,5-dichlorophenyl)-2-(3-methylpiperidino)propanone, the free base of CRL 41 419].

The arterial blood pressure, the heart and respiratory rates, the femoral arterial flow, the vertebral arterial flow and the rectal and cutaneous temperatures are measured. The coloration of the skin is observed. The blood gases are also determined in one of the three dogs.

It is found that CRL 41 419 administered in successive doses of 0.55 to 22 mg/kg I.D.
increases:
   the femoral flow rates in 2 out of 3 dogs from the dose of 5.5 mg/kg and in 3 out of 3 dogs at the dose of 11 mg/kg,
   the vertebral flow rate in 2 out of 3 dogs from the dose of 11 mg/kg,
   the heart rate at the dose of 22 mg/kg,
   the rectal ($+1.2°$ C.) and cutaneous ($+1.5°$ C.) temperatures,
   the dissolved $O_2$ supply at the dose of 22 mg/kg, and the production of $CO_2$ at the dose of 22 mg/kg;
lowers:
   the vertebral and femoral vascular resistances,
   the respiratory rate, and
   the arterial and venous pH, especially at the dose of 22 mg/kg;
does not change:
   the arterial blood pressure; and
causes:
   reddening of the skin from the dose of 22 mg/kg.

II. Intravenous Administration

At the end of the study under point I above, carried out by I.D. administration, the three dogs used above receive a single dose of 4.4 mg/kg of CRL 41 419 administered intravenously. It is found that on I.V. administration CRL 41 419
increases:
   the femoral flow rates (average change of $+189$ %) in the 3 dogs,
   the heart rate,
   the vertebral flow rate (average change of $+94$ % in 2 out of 3 dogs), and
   the rectal and cutaneous temperatures;
lowers:
   the femoral and vertebral resistances, and
   the respiratory rate; and
does not change:
   the arterial blood pressure; and
   the coloration of the skin.

III. Action on the Perfusion Pressure of the Hindquarters of Rats

The action of CRL 41 419 on the perfusion pressure of the hindquarters of rats was evaluated.

Groups of 10 male adult rats each (one control group and one group per dose of product to be tested) are subjected to the following working protocol. The rectal temperature of nembutal-anaesthetized rats is kept between 36.5° C. and 37.5° C. by means of a lamp and the perfusion pressure of the hindquarters, perfused through the abdominal aorta below the kidneys, is measured at a constant flow rate (5 ml/min) with an aerated and heated nutrient fluid. Each animal is then sacrificed by intravenous injection of KCl. The action of a series of 4 intravenous injections of 0.1 ml of 9 g/l NaCl isotonic solution or of 4 increasing doses of CRL 41 419 administered I.A. (non-cumulative) in solution in distilled water on the perfusion pressure increased by continuous perfusion in the liquid of noradrenaline hydrochloride (9 micrograms/minute) is evaluated. The treatments (9 g/l NaCl or CRL 41 419) are carried out randomly on the two groups of treated animals.

It is found that, at all the doses which were used (0.01 to 10 mg) CRL 41 419 lowers the perfusion pressure of the hindquarters of rats, while the said pressure had been increased by noradrenaline hydrochloride. The lowering in the perfusion pressure is statistically significant with regard (i) to the effects of 9 g/l NaCl and (ii) with respect to the control group.

It is also found that the intensity and the duration of action of CRL 41 419 increases proportionally with the doses used. After I.A. administration of 10 mg of CRL 41 419, the so-called demi-return time is 435 seconds.

All of these results show the vasodilative properties of CRL 41 419, which are evaluated objectively in particular by the increase in the Oz supply, on the one hand, and the fact that the arterial blood pressures are not changed in studies I and II above, on the other hand.

B. STUDIES RELATING TO CRL 41 418 (PRODUCT FROM EXAMPLE 2)

The toxicological and neuropsychopharmacological studies on CRL 41 418 were undertaken using the working methods described above for CRL 41 419, the CRL 41 418 to be studied being administered intraperitoneally in solution in distilled water, at pH 5.5, in a volume of 20 ml/kg to male mice and of 5 ml/kg to male rats.

Toxicological Study

Toxicity

The LD-0 of CRL 41 418 is higher than 128 mg/kg and the LD-100 of the said CRL 41 418 is of the order of kg administered intraperitoneally.

Neuropsychopharmacological Study

Overall Behaviour and Reactivities

The following are observed:

1) in mice
   for doses of 1 mg/kg, 4 mg/kg and 16 mg/kg:
   behaviour and reactivities substantially comparable to those of the control group; for a dose of 64 mg/kg:
   sedation;
   a lowering in the respiratory rate for 0.5 h,
   hypothermia for 3 h (maximum variation of $-2.8°$ C., 30 minutes after administration of CRL 41 418); and
   a lowering in the respiratory rate; and 2) in rats
   for doses of 0.5 mg/kg, 2 mg/kg and 8 mg/kg:
   behaviour, reactivities and a variation in the rectal temperature and in the pupil diameter substantially comparable to those of the control group; and
   for the dose of 32 mg/kg:
   moderate mydriasis for 1 h,
   hypothermia for 1 h (maximum variation: $-1.2°$ C., 30 minutes after administration of CRL 41 419); and
   a reduction in the reactivity to the touch and in the muscular tonus for 0.5 h.

Cardiovascular Study

In the cardiovascular study CRL 41 418 was administered I.D. in solution in 9 g/l NaCl solution (maximum concentration of CRL 41 418 used: 62 g/l, at pH 3).

Three male dogs (average weight: 12.1 kg each) anaesthetized with nembutal receive CRL 41 418 intraduodenally in successive doses of 0 (each animal serving as control with respect to itself); 0.5 mg/kg; 1 mg/kg; 2.5 mg/kg; 10 mg/kg and 20 mg/kg. The working protocol is that indicated above for CRL 41 419.

It is found that CRL 41 418 administered I.D. in doses of 0.5 to 20 mg/kg
increases
   the heart rate from the dose of 2.5 mg/kg,
   the vertebral flow rate in the 3 dogs from the dose of 2.5 mg/kg,
   the cutaneous temperature substantially and the rectal temperature very moderately,
   the differential pressure,
   the systolic pressure,
   the respiratory rate,
   the $O_2$ supply at the vertebral level and, to a much lesser extent, the consumption of $O_2$ (in 2 out of 3 dogs) estimated in general;

does not change:
   the diastolic and mean arterial blood pressures.

With respect to isoprenaline (administered intravenously in the dose of 1 μg/kg), CRL 41 418, administered I.D. in the cumulative dose of 39 mg/kg I.D. lowers: (i.e. partially opposes):
   the diastolic hypotension induced by isoprenaline [variation of $+40$ mm Hg (i.e. about $4.33 \times 10^3$ Pa) to $+76$ mm Hg (i.e. about $9.33 \times 10^4$ Pa) in the diastolic pressure]and
does not lower:
   overall, the tachycardia induced by isoprenaline [only a reduction in the variation of the order of $-23$ beats/minute to $-68$ beats/minute is observed].

With respect to noradrenaline (administered intravenously in the dose of 2 μg/kg), it is found that CRL 41 418, in the cumulative dose of 39 mg/kg I.D. reduces:
   the systolic hypertension induced by noradrenaline.

Moreover, propanolol (1 mg/kg I.V.) perfused for 6 minutes at the end of the experiment lowers the arterial blood pressure and the heart rate in 2 out of 2 dogs and lowers only the vertebral flow rate in one out of two dogs.

The results of these studies demonstrate that CRL 41 418 acts as a vasodilator. The tachycardia observed is due to a stimulation of the beta-adrenergic receptors because it is suppressed by propanolol.

C. COMPARATIVE STUDIES WITH CRL 41 240 AND CRLL 41 241

Studies analogous to those described for CRL 41 419 were carried out on anaesthetized dogs using CRL 41 240 and CRL 41 241.

Administered I.D. in doses of 0.1 to 20 mg/kg, CRL 41 240 and 41 241 proved devoid of an effect on the vertebral and femoral flow rates.

In clinical medicine, good results have been obtained by administering CRL 41 419 as a coronary vasodilator, on the one hand, and as a peripheral vasodilator, on the other hand, to adult man. In particular, CRL 41 419 has proved to be an excellent vasodilator at the daily dose of 200 to 300 mg (divided into two to three amounts of 100 mg each to be taken in the form of tablets or capsules), in particular for patients suffering from circulatory disorders in the region of the brain and in the region of the extremities.

I claim:

1. A compound selected from:
   (a) the compound corresponding to the general formula

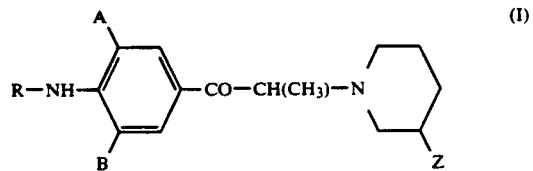

(I)

where R is H or $CH_3CO$, A is H or Cl, B, independently of A, is H or Cl and Z is a $C_1$-$C_4$-alkyl group; and
   (b) their addition salts.

2. Compound according to claim 1, in which $A=B=Cl$.

3. Compound according to claim 1, in which R = H or CH₃CO, A = B = Cl and Z = CH₃.

4. 1-(4-acetylamino-3,5-dichlorophenyl)-2-(3-methylpiperidino)propanone and its addition salts.

5. 1-(4-amino-3,5-dichlorophenyl)-2-(3-methylpiperidino)propanone and its addition salts.

6. A therapeutic composition having a vasodilative activity, comprising an effective amount of a compound selected from the compounds of formula I according to claim 1 and their non-toxic addition salts and a pharmaceutically acceptable excipient.

7. A method for treating the circulation disorders which comprises administering to a human in need thereof a compound selected from:
  (i) 1-(4-acetylamino-3,5-dichlorophenyl)-2-(3-methylpiperidino)propanone, (ii) 1-(4-amino-3,5-dichlorophenyl)-2-(3-methylpiperidino)propanone and (iii) their non-toxic addition salts.

8. A method for treating the circulation disorders of the brain and the extremities, which comprises administering to a human in need thereof a compound selected from 1-(4-acetylamino-3,5-dichlorophenyl)-2-(3-methyl-piperidino)propanone and its non-toxic addition salts.

9. A compound according to claim 1, wherein R is H.

10. A compound according to claim 1, wherein R is CH₃CO.

* * * * *